(12) United States Patent
Ziegler et al.

(10) Patent No.: US 8,657,778 B2
(45) Date of Patent: Feb. 25, 2014

(54) CASSETTE FOR USE IN A MEDICATION DELIVERY FLOW SENSOR ASSEMBLY AND METHOD OF MAKING THE SAME

(75) Inventors: John S. Ziegler, Arlington Heights, IL (US); James D. Morrow, Oak Lawn, IL (US); Olivier F. Currat, Chicago, IL (US); Jeff D. Bransky, Chicago, IL (US); Brian Barclay, Pleasanton Prairie, WI (US); Marwan A. Fathallah, Mundelein, IL (US); James D. Jacobson, Lindenhurst, IL (US)

(73) Assignee: Hospira, Inc., Lake Forest, IL (US)

( * ) Notice: Subject to any disclaimer, the term of this patent is extended or adjusted under 35 U.S.C. 154(b) by 404 days.

(21) Appl. No.: 12/842,168

(22) Filed: Jul. 23, 2010

(65) Prior Publication Data

US 2010/0286599 A1  Nov. 11, 2010

Related U.S. Application Data

(62) Division of application No. 12/469,459, filed on May 20, 2009, now Pat. No. 7,819,838.

(60) Provisional application No. 61/093,630, filed on Sep. 2, 2008.

(51) Int. Cl.
*A61M 31/00* (2006.01)

(52) U.S. Cl.
USPC ............... 604/65; 604/66; 604/67; 604/250; 417/413.1; 417/63

(58) Field of Classification Search
USPC .................. 604/65–67, 250; 417/413.1, 63; 73/861.52, 861.61
See application file for complete search history.

(56) References Cited

U.S. PATENT DOCUMENTS 4,195,515 A * 4/1980 Smoll ..................... 73/861.13
4,240,294 A   12/1980 Grande (Continued)

FOREIGN PATENT DOCUMENTS

JP    02093917 U    7/1990
JP    2007071695    3/2007

(Continued)

OTHER PUBLICATIONS

Alan F. Merry, Craig S. Webster and Daniel J. Matthew et al. A New Safety-Oriented Integrated Drug Administration and Automated Anesthesia Record System. Anesth Analg 2001 ;93:385-90.

(Continued)

*Primary Examiner* — Bhisma Mehta
*Assistant Examiner* — Matthew A Engel
(74) *Attorney, Agent, or Firm* — Michael R. Crabb

(57) ABSTRACT

A disposable assembly for use with a sensor assembly comprises a body, a flow restricting element, and a fluid pressure membrane. The body has a lid portion and a base portion. The body defines a fluid flow passage that forms an inlet and an outlet. The flow restricting element is positioned in the fluid flow passage between the inlet and the outlet. The membrane is located between the lid and base portions along the fluid flow passage. A reinforcing structure, such as a ring or a rigid disk, is positioned between the fluid pressure membrane and the lid portion to provide increased resistance to pressure in the fluid flow passage. The ring or disk can be a separate component or formed on the membrane. The membrane thickness adjacent to sensor access openings in the lid portion can be increased for pressure resistance, too.

8 Claims, 16 Drawing Sheets

(56) References Cited

U.S. PATENT DOCUMENTS

| | | | |
|---|---|---|---|
| 4,261,356 A | 4/1981 | Turner et al. | |
| 4,343,316 A | 8/1982 | Jespersen | |
| 4,626,244 A | 12/1986 | Reinicke | |
| 4,694,273 A | 9/1987 | Franchino | |
| 4,758,228 A | 7/1988 | Williams | |
| 4,856,339 A | 8/1989 | Williams | |
| 4,881,413 A | 11/1989 | Georgi et al. | |
| 4,892,656 A | 1/1990 | Pietzsch | |
| 4,938,079 A | 7/1990 | Goldberg | |
| 4,947,856 A | 8/1990 | Beard | |
| 5,211,626 A | 5/1993 | Frank et al. | |
| 5,242,406 A | 9/1993 | Gross et al. | |
| 5,287,851 A | 2/1994 | Beran et al. | |
| 5,325,728 A | 7/1994 | Zimmerman et al. | |
| 5,417,119 A | 5/1995 | Smoll | |
| 5,417,395 A | 5/1995 | Fowler et al. | |
| 5,450,758 A | 9/1995 | Smoll | |
| 5,463,906 A | 11/1995 | Spani et al. | |
| 5,611,784 A | 3/1997 | Barresi et al. | |
| 5,628,309 A | 5/1997 | Brown | |
| 5,651,775 A | 7/1997 | Walker et al. | |
| 5,672,832 A * | 9/1997 | Cucci et al. | 73/861.52 |
| 5,697,916 A | 12/1997 | Schraga | |
| 5,728,074 A | 3/1998 | Castellano et al. | |
| 5,752,918 A | 5/1998 | Fowler et al. | |
| 5,758,643 A | 6/1998 | Wong et al. | |
| 5,805,455 A | 9/1998 | Lipps | |
| 5,848,971 A * | 12/1998 | Fowler et al. | 600/486 |
| 5,891,051 A | 4/1999 | Han et al. | |
| 5,904,666 A | 5/1999 | DeDecker et al. | |
| 5,944,660 A | 8/1999 | Kimball et al. | |
| 5,947,911 A | 9/1999 | Wong et al. | |
| 6,032,536 A | 3/2000 | Peeters et al. | |
| 6,068,615 A | 5/2000 | Brown et al. | |
| 6,237,398 B1 | 5/2001 | Porat et al. | |
| 6,250,132 B1 | 6/2001 | Drzewiecki | |
| 6,270,455 B1 | 8/2001 | Brown | |
| 6,272,934 B1 | 8/2001 | Rajan et al. | |
| 6,277,099 B1 | 8/2001 | Strowe et al. | |
| 6,349,740 B1 | 2/2002 | Cho et al. | |
| 6,385,505 B1 | 5/2002 | Lipps | |
| 6,386,050 B1 | 5/2002 | Yin et al. | |
| 6,445,053 B1 | 9/2002 | Cho | |
| 6,482,185 B1 | 11/2002 | Hartmann | |
| 6,558,125 B1 | 5/2003 | Futterknecht | |
| 6,568,416 B2 | 5/2003 | Tucker et al. | |
| 6,578,435 B2 | 6/2003 | Gould et al. | |
| RE38,189 E | 7/2003 | Walker et al. | |
| 6,609,047 B1 | 8/2003 | Lipps | |
| D481,121 S | 10/2003 | Evans | |
| D485,356 S | 1/2004 | Evans | |
| 6,685,668 B1 | 2/2004 | Cho et al. | |
| 6,685,678 B2 | 2/2004 | Evans et al. | |
| 6,700,784 B2 | 3/2004 | Huang et al. | |
| 6,722,211 B1 | 4/2004 | Ciobanu et al. | |
| 6,760,643 B2 | 7/2004 | Lipps | |
| 6,813,964 B1 | 11/2004 | Clark et al. | |
| 6,915,679 B2 * | 7/2005 | Chien et al. | 73/54.01 |
| 6,920,795 B2 * | 7/2005 | Bischoff et al. | 73/706 |
| 6,929,619 B2 | 8/2005 | Fago et al. | |
| 6,932,796 B2 | 8/2005 | Sage et al. | |
| 6,935,192 B2 | 8/2005 | Sobek et al. | |
| 6,964,204 B2 | 11/2005 | Clark et al. | |
| 6,975,922 B2 | 12/2005 | Duncan et al. | |
| 6,981,960 B2 | 1/2006 | Cho et al. | |
| 7,059,184 B2 | 6/2006 | Kanouola et al. | |
| 7,074,209 B2 | 7/2006 | Evans et al. | |
| 7,082,843 B2 | 8/2006 | Clark et al. | |
| 7,096,729 B2 | 8/2006 | Repko et al. | |
| 7,115,113 B2 | 10/2006 | Evans et al. | |
| 7,161,488 B2 | 1/2007 | Frasch | |
| 7,162,290 B1 | 1/2007 | Levin | |
| 7,162,927 B1 * | 1/2007 | Selvan et al. | 73/753 |
| 7,415,895 B2 | 8/2008 | Kurisaki et al. | |
| 7,503,903 B2 * | 3/2009 | Carlisle et al. | 604/67 |
| 7,571,024 B2 | 8/2009 | Duncan et al. | |
| 7,693,697 B2 | 4/2010 | Westenskow et al. | |
| 7,784,330 B2 * | 8/2010 | Angelescu et al. | 73/54.09 |
| 7,819,838 B2 | 10/2010 | Ziegler et al. | |
| 2002/0038392 A1 | 3/2002 | De La Huerga | |
| 2002/0099334 A1 | 7/2002 | Hanson et al. | |
| 2003/0065537 A1 | 4/2003 | Evans | |
| 2004/0082918 A1 | 4/2004 | Evans et al. | |
| 2004/0225409 A1 | 11/2004 | Duncan et al. | |
| 2004/0232219 A1 | 11/2004 | Fowler | |
| 2004/0251406 A1 | 12/2004 | Figueria | |
| 2006/0142692 A1 | 6/2006 | Jacobson et al. | |
| 2006/0181695 A1 | 8/2006 | Sage, Jr. | |
| 2006/0260416 A1 | 11/2006 | Sage et al. | |
| 2006/0266128 A1 | 11/2006 | Clark et al. | |
| 2007/0060872 A1 | 3/2007 | Hall et al. | |
| 2007/0129618 A1 | 6/2007 | Goldberger et al. | |
| 2007/0179436 A1 | 8/2007 | Braig et al. | |
| 2009/0004767 A1 | 1/2009 | Parks et al. | |
| 2009/0157040 A1 | 6/2009 | Jacobson et al. | |

FOREIGN PATENT DOCUMENTS

| | | |
|---|---|---|
| WO | 200227276 A2 | 4/2002 |
| WO | 2005082450 A1 | 9/2005 |
| WO | 2005118015 A1 | 12/2005 |

OTHER PUBLICATIONS

Dec. 2005 Advertisement from SensorONE Ltd for the Series PD-39 X Differential Pressure Transmitter.
2005 Advertisement from BARD for the CritiCore Monitor.

* cited by examiner

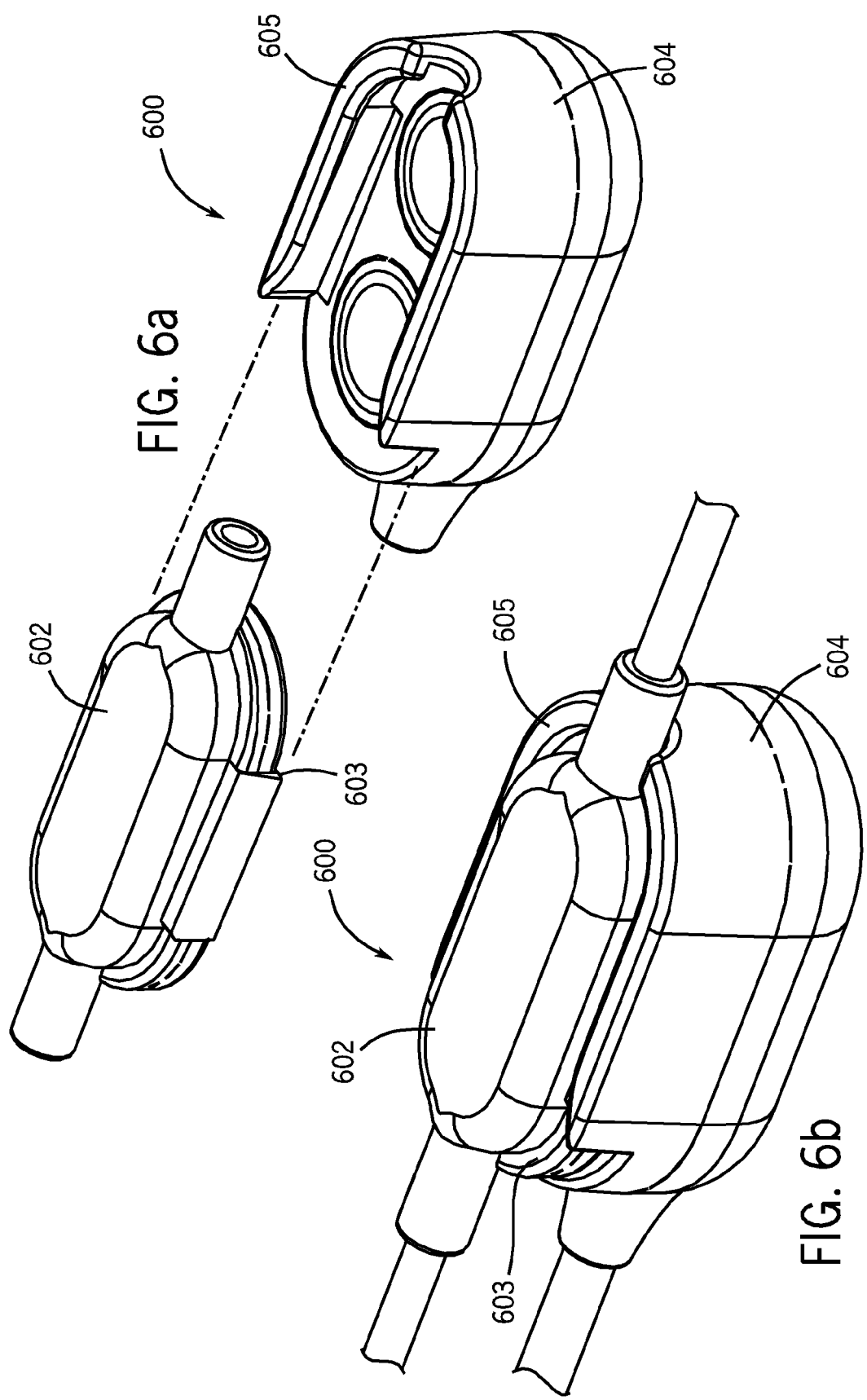

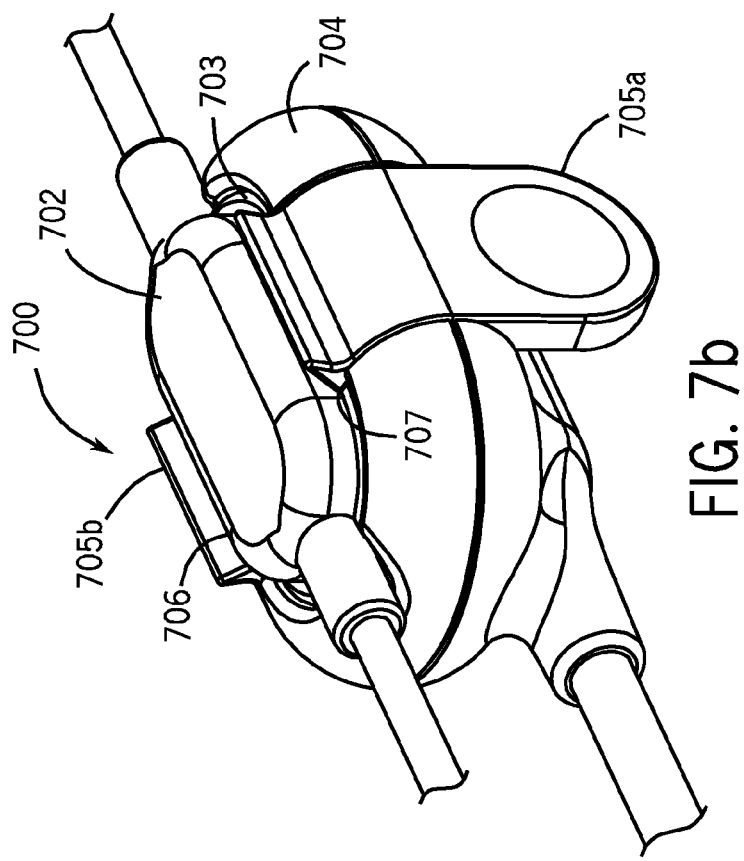
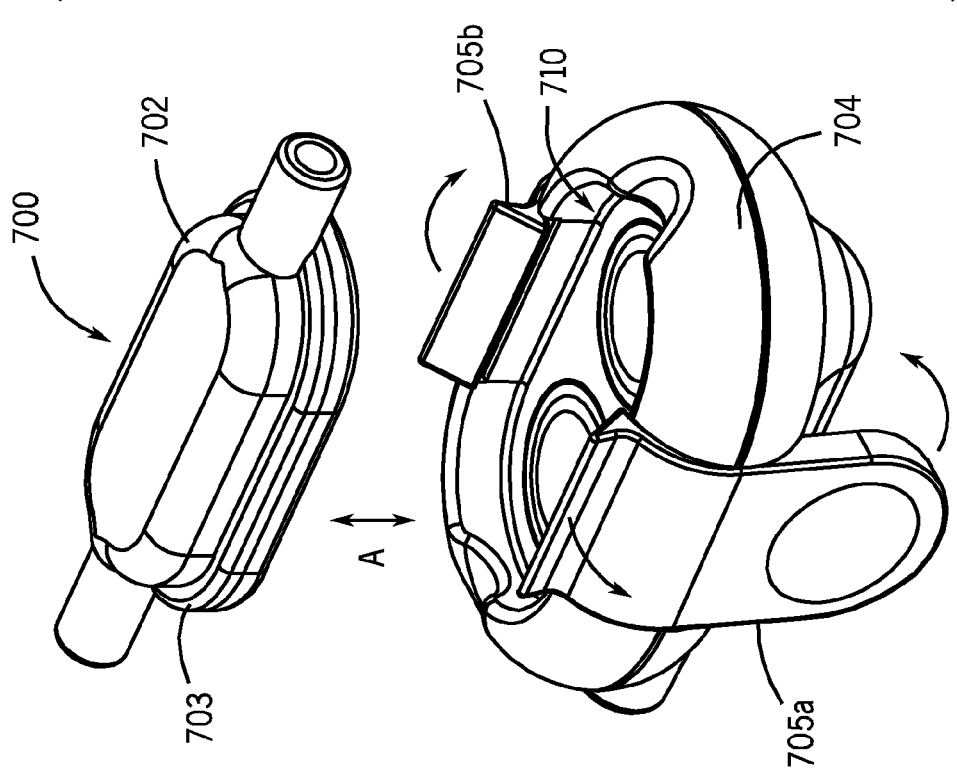
FIG. 7b
FIG. 7a

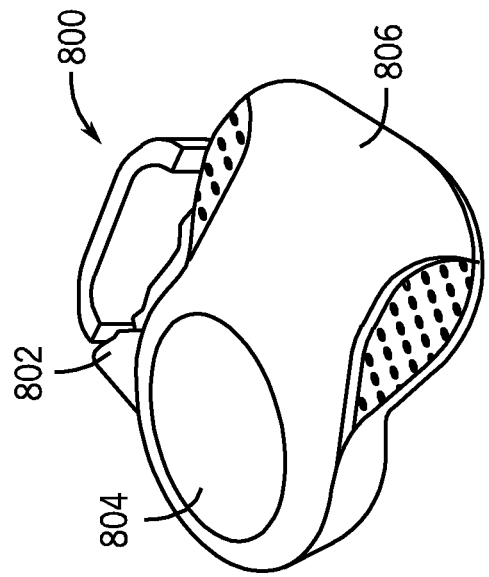
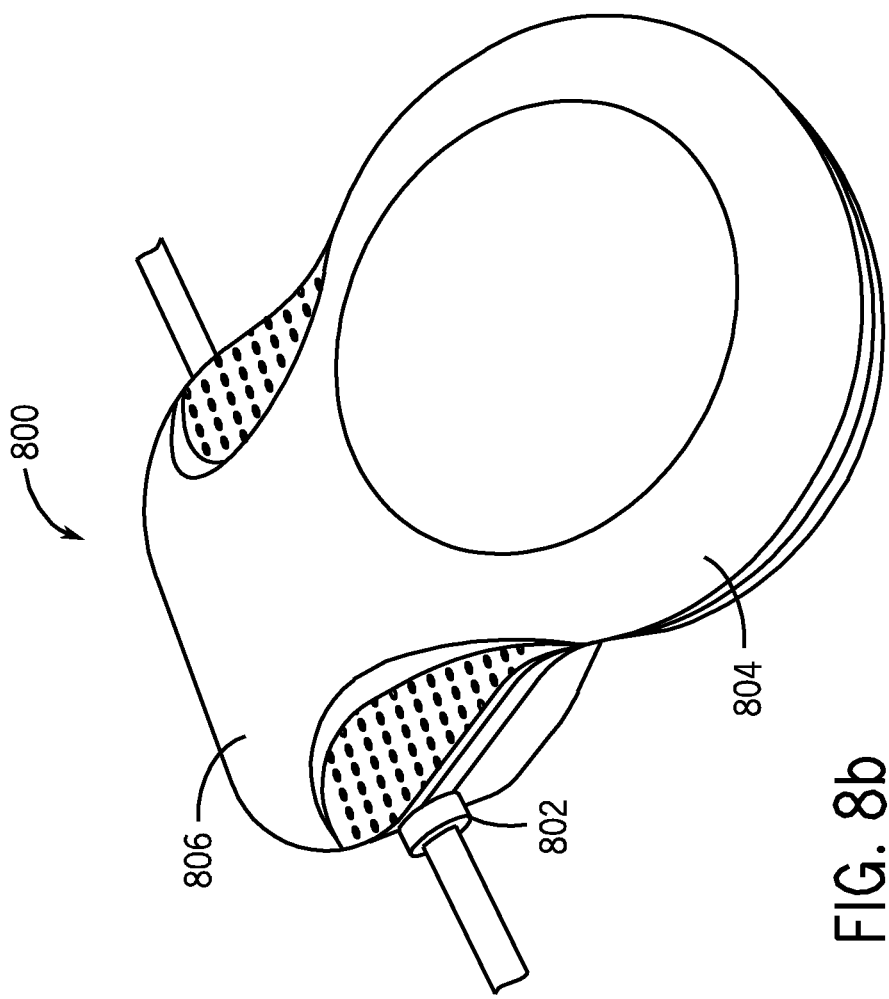

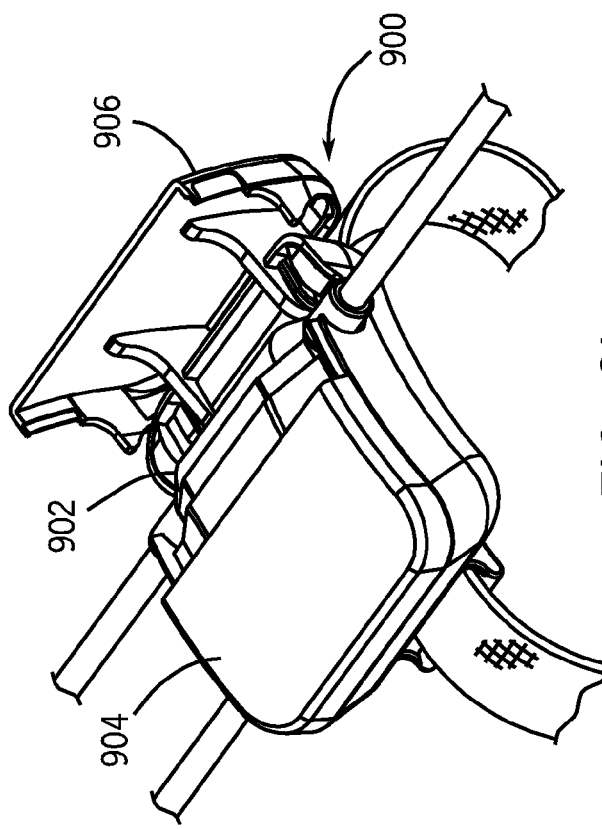
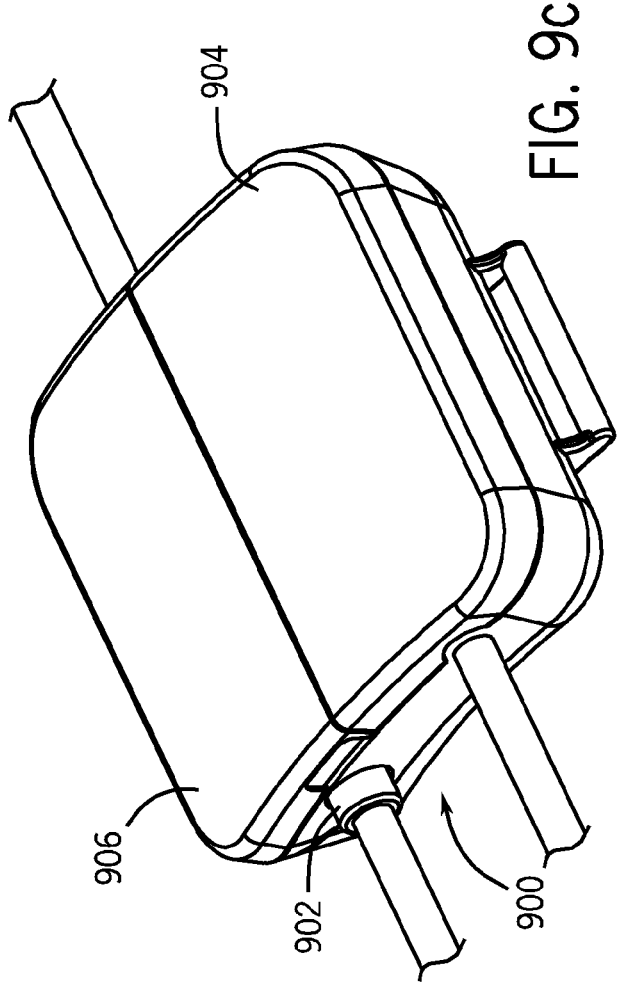

US 8,657,778 B2

CASSETTE FOR USE IN A MEDICATION DELIVERY FLOW SENSOR ASSEMBLY AND METHOD OF MAKING THE SAME

CROSS REFERENCE TO RELATED APPLICATIONS

This application is a divisional of U.S. patent application Ser. No. 12/469,459, filed on May 20, 2009, now U.S. Pat. No. 7,819,838, which claims priority under 35 U.S.C. 119 to U.S. Ser. No. 61/093,630 filed Sep. 2, 2008, the disclosures of which are hereby incorporated by reference as if set forth in full herein.

TECHNICAL FIELD

The present invention generally relates to a cassette through which medication is delivered. In particular, the cassette is used in a differential pressure based flow sensor assembly and method for monitoring medication delivery utilizing a system containing the differential pressure based flow sensor assembly, and more particularly to a differential pressure based flow sensor assembly that has a disposable portion and a reusable portion. More particularly, the present invention relates to a cassette that serves as the disposable portion of such a flow sensor assembly and is capable of withstanding fluid pressures greater than conventional cassettes. The present invention also relates to methods of making a high pressure capacity cassette.

BACKGROUND

Modern medical devices, including medical pumps, are increasingly being controlled by microprocessor based systems to deliver fluids, solutions, medications, and drugs to patients. A typical control for a medical pump includes a user interface enabling a medical practitioner to enter the dosage of fluid to be delivered, the rate of fluid delivery, the duration, and the volume of a fluid to be infused into a patient. Typically, drug delivery is programmed to occur as a continuous infusion or as a single bolus dose.

It is common for a plurality of medications to be infused to a patient by using a multi-channel infusion pump or using a plurality of single channel infusion pumps where a different fluid is administered from each channel. Another method of delivering multiple medications to a patient is to deliver a first medication using an infusion pump, and additional medications through single bolus doses.

When delivering medications through single bolus doses it is important to verify that correct medications are being delivered to the patient as well to verify that the correct amount of medication is being delivered to the patient. Typically a caregiver simply manually notes on the patient's paper chart the amount of medication delivered via a bolus dose, and that information may later be entered into a patient's record electronically. Thus, human error may lead to an accidental overdose or underdose of a medication, while a caregiver believes that a proper dose was delivered. In addition to an error in medication dosing, it is also possible that human error may result in the failure to record the medication delivered during a single bolus dose. Thus, it is possible that a patient's medical records may not reflect every medication that patient has been given. A sensor within the IV line capable of measuring a wide range of fluids and flow rates would be helpful in documenting the flow rate and volume of every medication the patient is given through that line. Further, it is desirable to provide a robust flow rate sensing methodology that is low cost and in particular introduces low incremental cost to the disposable medication delivery tubing set. Further, it is desirable to provide a flow rate sensing methodology that is capable of accurately sensing the flow rate of fluids that have a range of physical properties, including fluid viscosity, which may not be known precisely. It also may occur that the fluid pressure in a disposable portion or cassette of the flow sensor is higher than normal conditions that conventional cassettes might experience in traditional use. Therefore, a need exists for a cassette for use in a differential pressure based flow sensor system adapted for monitoring medication delivery that is also capable of withstanding higher pressures without failure.

SUMMARY

According to one embodiment, a disposable assembly for use with a flow sensor assembly comprises a body, a flow restricting element, a fluid pressure membrane, a first reinforcing ring, and a second reinforcing ring. The body has a lid portion and a base portion. The body defines a fluid flow passage that forms an inlet and an outlet. The lid portion has a first opening and a second opening. The flow restricting element is positioned in the fluid flow passage between the inlet and the outlet and between the first opening and the second opening. The fluid pressure membrane is disposed along the fluid flow passage between the inlet and the outlet. The fluid pressure membrane is located between the lid portion and the base portion of the body so as to be accessible for sensing purposes at the first opening and the second opening of the lid portion. The first reinforcing ring surrounds a portion of the fluid pressure membrane adjacent to the first opening of the lid portion. The first reinforcing ring is positioned between the lid portion and the fluid pressure membrane. The second reinforcing ring surrounds a portion of the fluid pressure membrane adjacent to the second opening of the lid portion. The second reinforcing ring is positioned between the lid portion and the fluid pressure membrane. The disposable assembly defines a high pressure cassette for medication delivery.

According to another embodiment, a disposable assembly for use with a flow sensor assembly comprises a body, a flow restricting element, a fluid pressure membrane, a first rigid disk, and a second rigid disk. The body has a lid portion and a base portion. The body defines a fluid flow passage that forms an inlet and an outlet. The lid portion has a first opening and a second opening. The flow restricting element is positioned in the fluid flow passage between the inlet and the outlet. The fluid pressure membrane is disposed along the fluid flow passage between the inlet and the outlet. The fluid pressure membrane can define an opening that receives the flow restricting element. The fluid pressure membrane is located between the lid portion and the base portion of the body. The first rigid disk is positioned between the fluid pressure membrane and the lid portion adjacent to the first opening of the lid portion. The second rigid disk is positioned between the fluid pressure membrane and the lid portion adjacent to the second opening of the lid portion.

According to one method a differential pressure based fluid flow sensor assembly is formed. The method provides a reusable assembly that comprises at least a first pressure sensor and a second pressure sensor. A disposable assembly is also provided. The disposable assembly has a body, a flow restricting element, a fluid pressure membrane, a first rigid disk, and a second rigid disk. The body has a lid portion and a base portion. The body defines a fluid flow passage that forms an inlet and an outlet. The lid portion has a first opening and a second opening. The flow restricting element is positioned in the fluid flow passage between the inlet and the outlet. The fluid pressure membrane is disposed along the fluid flow passage between the inlet and the outlet. The fluid pressure membrane can define an opening that receives the flow restricting element. The fluid pressure membrane is located between the lid portion and the base portion of the body. The first rigid disk is positioned between the fluid pressure membrane and the lid portion adjacent to the first opening of the lid portion. The second rigid disk is positioned between the fluid pressure membrane and the lid portion adjacent to the second opening of the lid portion. The disposable assembly is coupled with or secured to the reusable assembly in a removable manner to form a differential pressure based fluid pressure sensor.

BRIEF DESCRIPTION OF THE DRAWINGS

FIG. 6a schematically illustrates a method of assembling a differential pressure based flow sensor assembly according to one embodiment;

FIG. 6b schematically illustrates an assembled differential pressure based flow sensor assembly according to the embodiment of FIG. 6a;

FIG. 7a schematically illustrates a method of assembling a differential pressure based flow sensor assembly according to another embodiment;

FIG. 7b schematically illustrates an assembled differential pressure based flow sensor assembly according to the embodiment of FIG. 7a;

FIG. 8a schematically illustrates a method of assembling a differential pressure based flow sensor assembly according to a further embodiment;

FIG. 8b schematically illustrates an assembled differential pressure based flow sensor assembly according to the embodiment of FIG. 8a;

FIG. 8c schematically illustrates an exploded view of the differential pressure based flow sensor assembly according to the embodiment of FIG. 8a;

FIG. 9b schematically illustrates an assembled differential pressure based flow sensor assembly with an access door open according to the embodiment of FIG. 9a;

FIG. 9c schematically illustrates an assembled differential pressure based flow sensor assembly with an access door closed according to the embodiment of FIG. 9a;

FIG. 10b schematically illustrates an assembled differential pressure based flow sensor assembly according to the embodiment of FIG. 10a;

DETAILED DESCRIPTION

Figure 1:
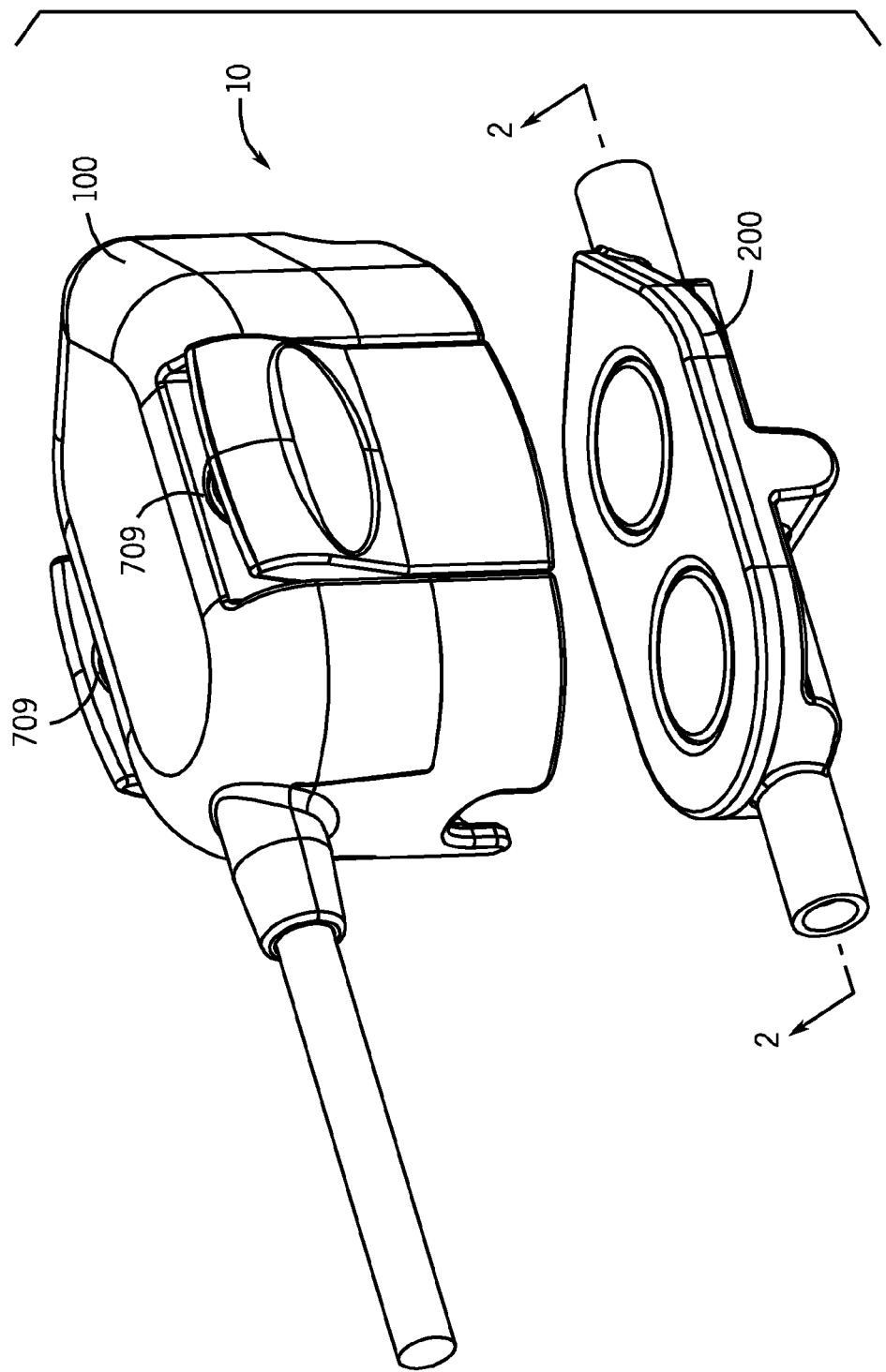
FIG. 1 is a pictorial view that illustrates a differential pressure based flow sensor assembly with a reusable portion and a disposable portion in a decoupled state according to one embodiment.

While this invention is susceptible of embodiments in many different forms, there is shown in the drawings and will herein be described an example of the invention. The present disclosure is to be considered as an example of the principles of the invention. It is not intended to limit the broad aspect of the invention to the examples illustrated.

FIG. 1 is a pictorial representation of a differential pressure based flow sensor assembly 10 in an unassembled state. The differential pressure based flow sensor assembly comprises a reusable portion 100 and a disposable portion 200 that may also be referred to herein as a cassette.

Figure 2:
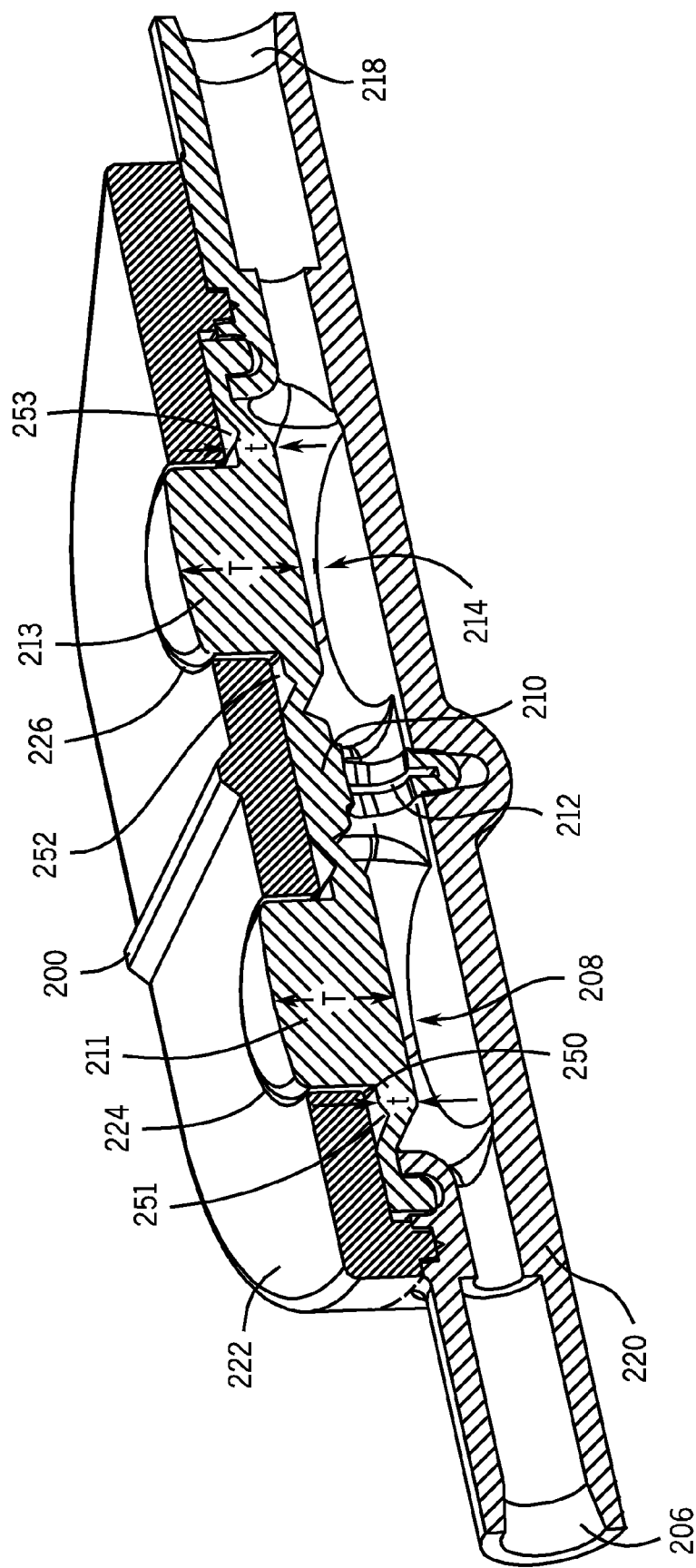
FIG. 2 shows a cross sectional view of the disposable portion of the embodiment shown in FIG. 1.

As better shown in FIG. 2, the disposable portion 200 comprises: a fluid inlet 206; an upstream fluid chamber 208; a fluid pressure membrane 210; a flow restricting element 212; a downstream fluid chamber 214; and a fluid outlet 218. The membrane 210 is fluid impermeable. The disposable portion 200 has a body that includes a base 220 and a lid 222 connected to the base 220. The body defines a fluid flow passage extending between the inlet 206 and the outlet 218, through the fluid chambers 208, 214. The membrane 210 is disposed along the fluid flow passage and sealingly covers the chambers 208, 214 to form movable pressure responsive wall portions responsive to the fluid pressure within the passage, particularly in the fluid chambers 208, 214. The flow restricting element 212 is positioned in the fluid flow passage between the inlet 206 and the outlet 208. In the embodiment shown, the flow restricting element 212 is a separate component from the lid 222 and the base 220 and is secured within the fluid pressure membrane.

Figure 3:
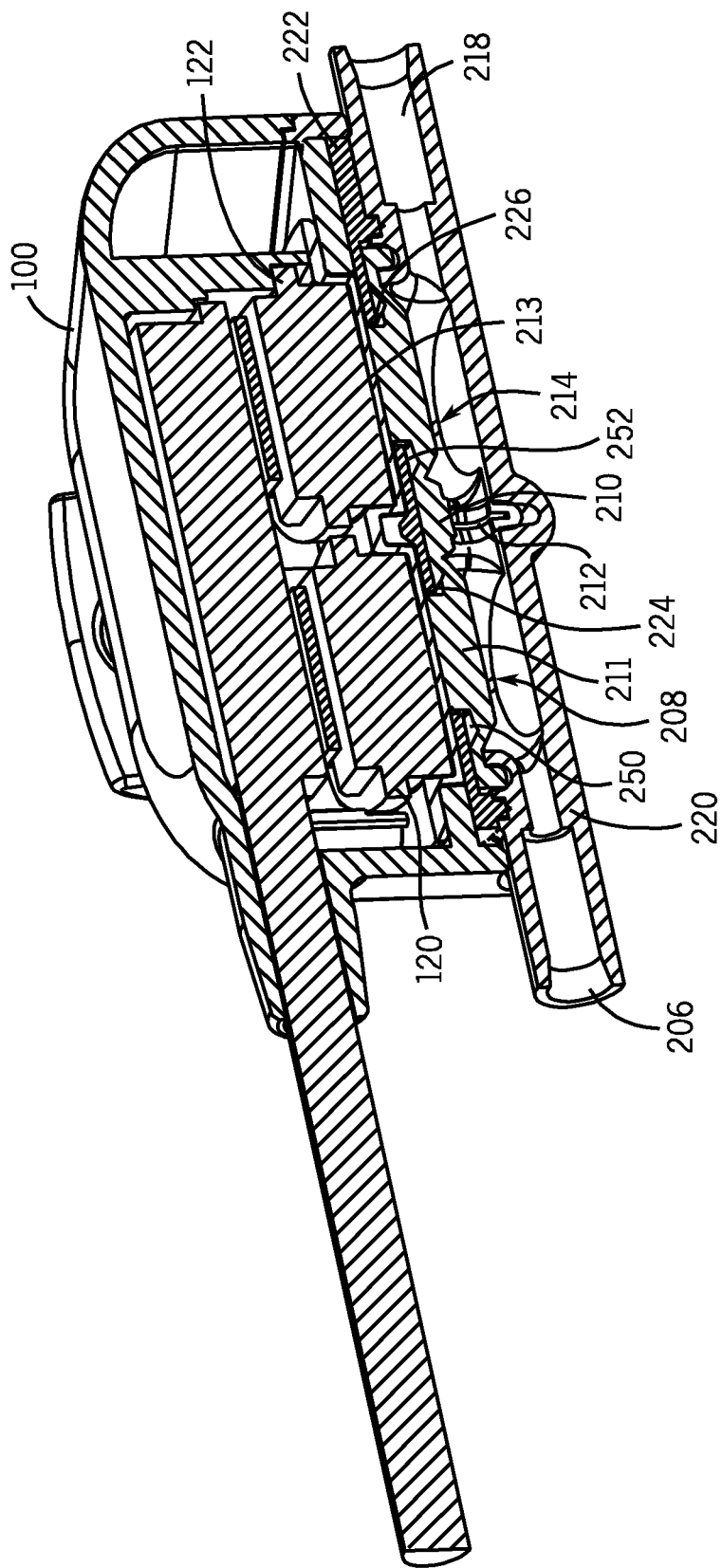
FIG. 3 is a cross sectional view of the differential pressure based flow sensor assembly of FIG. 1 in an assembled or coupled state taken along line 2-2 of FIG. 1.

As shown in FIGS. 1-3, medication, or some other fluid, enters the disposable portion 200 through the fluid inlet 206. The medication flows into the upstream fluid chamber 208 from the fluid inlet 206. Next, the medication flows through the flow restricting element 212 and into the downstream fluid chamber 214. The flow of the medication through the flow restricting element 212 results in a drop in fluid pressure as the fluid flows from the upstream fluid chamber 208 to the downstream fluid chamber 214 through the flow restricting element 212. Thus, during forward fluid flow under normal conditions, the fluid pressure within the upstream fluid chamber 208 is generally greater the fluid pressure within the downstream fluid chamber 214. The fluid pressure within the upstream fluid chamber 208 presses against a first area 211 of the fluid pressure membrane 210. Similarly, the fluid pressure within the downstream fluid chamber 214 presses against a second area 213 of the fluid pressure membrane 210.

The lid 222 forms an upstream opening 224 and a downstream opening 226 aligned with the first and second areas 211, 213 respectively. The openings 224, 226 allow the first and second areas 211, 213 of the fluid pressure membrane 210 to communicate, respectively, with the upstream pressure sensor 120 and the downstream pressure sensor 122 of the reusable portion 100. The flow restricting element 212 is at least operatively positioned between the openings 224, 226. The first and second areas 211, 213 optionally may be raised to extend into or more preferably through the openings 224, 226 to engage the sensors 120, 122. Raising the first and second areas 211, 213 additionally aids in the positioning of the lid 222 and the membrane 210 during assembly.

The lid 222 is positioned such that the fluid pressure membrane 210 is positioned between the base 220 and the lid 222. The lid 222 and the base 220 may be ultrasonically welded together to form a fully assembled sealed disposable portion 200, as viewed in FIG. 1. The fluid pressure membrane 210 may thus be firmly sealingly secured between the base 220 and the lid 222 without the use of any adhesive to fasten the fluid pressure membrane 210 to either the base 220 or the lid 222.

As shown in FIGS. 1-3, the fluid pressure membrane 210 is a flexible diaphragm type membrane. The fluid pressure membrane 210 may be formed from silicone, or some other flexible polymeric material or elastomeric material. In FIGS. 2-3, the membrane 210 optionally has an increased wall thickness "T" defined between the top and bottom surfaces of the membrane 210 at the first and second areas 211, 213 in order to form thickened solid projections, heads or plugs to raise the fluid pressure at which the membrane 210 fails. The first and second areas 211, 213, or at least a portion thereof, have a thickness T greater than the thickness "t" in other areas of the membrane. The resulting solid projections, heads or plugs increase resistance to any pressure which may be applied. Thus, the increased thickness of the first and second areas 211, 213 provides additional strength to the membrane 210 in those areas, increasing the pressure level at which the membrane 210 will fail. Situations where the disposable portion 200 is subjected to higher fluid pressures than expected may include: a manual bolus dose that is provided too quickly; the disposable portion 200 not being used or coupled with the reusable portion 100, as may occur when a patient is being moved; an occlusion of the fluid pathway upstream or downstream from flow restricting element 212; or the disposable portion 200 not being properly positioned or securely coupled with the reusable portion 100.

In one embodiment, a reinforcing ring 250, 252 surrounds each of the first and second areas 211, 213. The rings 250, 252 are located between the membrane 210 and the lid 222 of the disposable portion 200. In one embodiment, the rings 250, 252 are each integrally formed as or defined by a rib on the membrane 210 as shown in FIGS. 2 and 3. In another embodiment, not shown but readily understood from the description herein, the rings 250, 252 can be separate components distinct from the membrane 210. In yet another embodiment that is not shown, the rings 250, 252 can be linked together and formed as a single support plate separate from the membrane. Referring again to the illustrated case where the reinforcing rings 250, 252 are integrally formed as ribs on the membrane 210, the ribs define raised annular areas of increased thickness on the membrane 210. Surrounding the rings 250, 252 are thinner annular regions 251, 253 respectively. As pressure is applied to the membrane 210 from within the fluid flow passage, the first and second areas 211, 213 of the membrane 210 are pushed upward toward, into, or through the openings 224, 226 of the lid 222. Flexing takes place primarily in the thinner annular regions 251, 253, allowing for greater sensitivity of pressure measurement. The rings 250, 252 contact the lid 222 if the membrane 210 is raised by the pressure of the fluid to a level that has been determined to exceed the measurement range of the sensor assembly. Once the rings 250, 252 contact the lid 222 the first and second areas 211, 213 of the membrane 210 are supported by the areas of the lid 222 surrounding the openings 224, 226 of the lid. The use of the rings 250, 252 allows the disposable portion 200 to withstand higher operating pressures, without causing the thickness of the membrane 210 in other areas to become so thick that sensitivity of the sensor assembly 10 is degraded.

The terms "ring" and "annular" are used broadly herein to refer to loop shapes in general. For example, an elliptical, oval or other type of ring or annular shape would not detract from the invention, especially if the openings 224, 226 and membrane areas 211, 213 are similarly shaped.

It is contemplated that a variety of materials may be utilized for the manufacture of the disposable portion 200. The disposable portion 200 may comprise a thermoplastic. It is contemplated that the flow restricting element 212 may be made of the same thermoplastic as the rest of the disposable portion 200, or may be a different material than the disposable portion 200. Non-limiting examples of the material that may be utilized to form the flow restricting element 212 include silicon, glass, and medical grade thermoplastics and elastomers. The flow restricting element 212 even can be made in whole or in part of stainless steel. A stainless steel orifice plate can be encased in a thermoplastic or elastomeric frame. The fluid pressure membrane 210 may comprise a variety of polymeric or elastomeric materials, such as TPE, or silicone. In one embodiment which will be understood in view of FIG. 4, the membrane has a fold therein that holds the flow restricting element and includes fluid passages 515a, 515b in fluid communication with the flow restricting element so that fluid may flow therethrough and between the upstream and downstream fluid chambers.

As shown in FIG. 3, medication enters the disposable portion 200 through the fluid inlet 206. The medication flows into the upstream fluid chamber 208 from the fluid inlet 206. Next, the medication flows through the flow restricting element 212 and into the downstream fluid chamber 214. The flow of the medication through the flow restricting element 212 results in a drop in fluid pressure as the fluid flows from the upstream fluid chamber 208 to the downstream fluid chamber 214 through the flow restricting element 212. Thus, during forward fluid flow under normal conditions, the fluid pressure within the upstream fluid chamber 208 is generally greater the fluid pressure within the downstream fluid chamber 214. The fluid pressure within the upstream fluid chamber 208 presses against the first area 211 of the fluid pressure membrane 210, causing the first area 211 of the membrane 210 to press against the upstream fluid pressure sensor 120 at the upstream opening 224 of the lid 222. In one embodiment, the second area 211 at least partially extends into the opening 224 of the lid 222. Similarly, the fluid pressure within the downstream fluid chamber 214 presses against the second area 213 of the fluid pressure membrane 210, causing the second area 213 of the membrane 210 to press against the downstream fluid pressure sensor 122 at the downstream opening 226 of the lid 222. In one embodiment, the second area 213 at least partially extends into the opening 226 of the lid 222.

Figure 4:
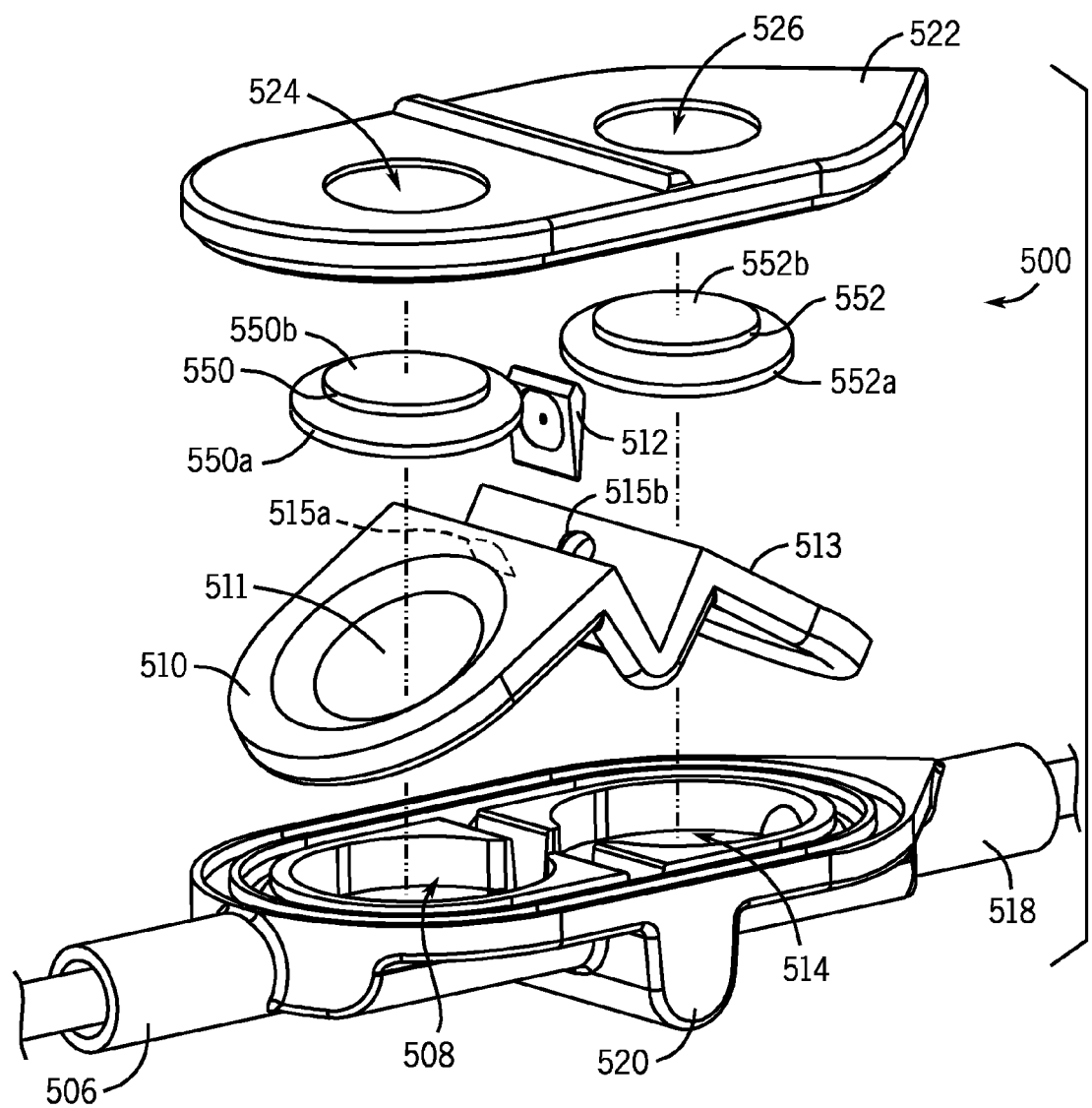
FIG. 4 is an exploded view of a disposable portion of a differential pressure based flow sensor assembly according to another embodiment.
Figure 5:
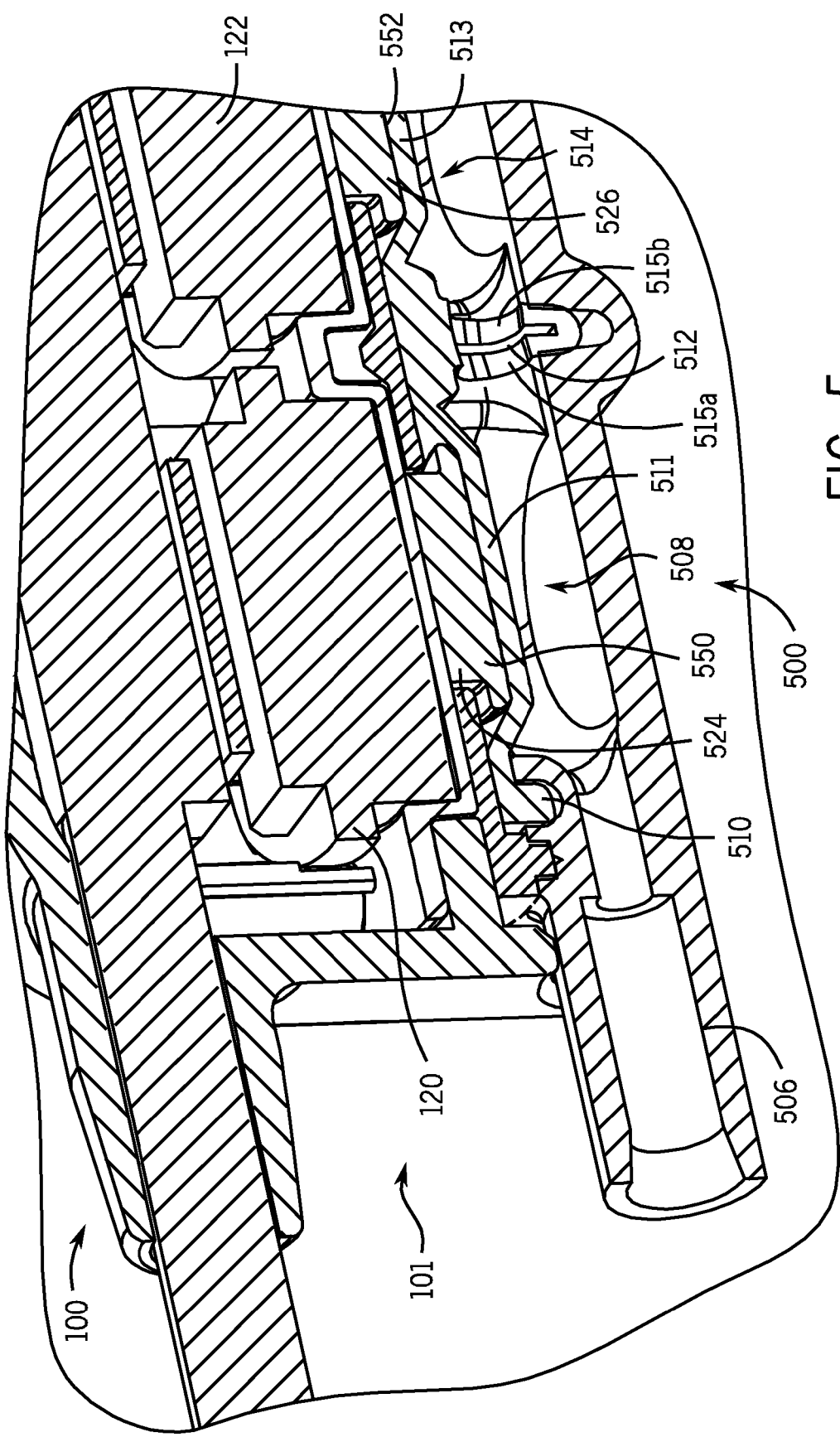
FIG. 5 is a partial cross sectional view of a differential pressure based flow sensor assembly having the disposable portion of FIG. 4.

FIG. 4 is an exploded pictorial representation of a disposable portion 500 for a differential pressure based flow sensor assembly 10' (FIG. 5). The differential pressure based flow sensor assembly 10' comprises the reusable portion 100 and the disposable portion 500.

The disposable portion 500 comprises: a fluid inlet 506; an upstream fluid chamber 508; a fluid pressure membrane 510; a flow restricting element 512; a downstream fluid chamber 514; and a fluid outlet 518. The membrane 510 is fluid impermeable. The disposable portion 502 has a base 520 and a lid 522. In one embodiment, the membrane 510 includes fluid passages 515a, 515b in fluid communication with the flow restricting element 512 so that fluid may flow therethrough and between the upstream and downstream fluid chambers 508, 514. The membrane 510 is disposed along the main fluid flow passage and sealingly covers the chambers 508, 514 to form movable pressure responsive wall portions responsive to the fluid pressure within the main fluid flow passage, particularly in the fluid chambers 508, 514.

As shown in FIGS. 4-5, medication, or some other fluid, enters the disposable portion 500 through the fluid inlet 506. The medication flows into the upstream fluid chamber 508 from the fluid inlet 506. Next, the medication flows through the flow restricting element 512 and into the downstream fluid chamber 514. The flow of the medication through the flow restricting element 512 results in a drop in fluid pressure as the fluid flows from the upstream fluid chamber 508 to the downstream fluid chamber 514 through the flow restricting element 512. Thus, during forward fluid flow under normal conditions, the fluid pressure within the upstream fluid chamber 508 is generally greater the fluid pressure within the downstream fluid chamber 514. The fluid pressure within the upstream fluid chamber 508 presses against a first area 511 of the fluid pressure membrane 510. Similarly, the fluid pressure within the downstream fluid chamber 514 presses against a second area 513 of the fluid pressure membrane 510.

The lid 522 forms an upstream opening 524 and a downstream opening 526 to allow the first and second areas 511, 513 of the fluid pressure membrane 510 to communicate, respectively, with the upstream pressure sensor 120 and the downstream pressure sensor 122 of the reusable portion 100.

The lid 522 is positioned such that the fluid pressure membrane 510 is positioned between the base 520 and the lid 522. The lid 522 and the base 520 may be ultrasonically welded together to form a fully assembled disposable portion 502, as viewed in FIG. 5. The fluid pressure membrane 510 may thus be firmly secured between the base 520 and the lid 522 without the use of any adhesive to fasten the fluid pressure membrane 510 to either the base 520 or the lid 522.

As shown in FIGS. 4-5, rigid disks 550, 552 are positioned above each of the first and second areas 511, 513 of the membrane 510 between the membrane 510 and the lid 522. Thus, as pressure is applied to the membrane 510, the first and second areas 511, 513 of the membrane 510 are pushed upward towards the openings 524, 526 of the lid 522, thus moving the rigid disks 550, 552 towards the openings 550, 552. The rigid disks 550, 552 contact the lid 522 as the membrane 510 is raised by the pressure of the fluid flow. Once the rigid disks 550, 552 contact the lid 522 the first and second areas 511, 513 of the membrane 510 are constrained and may not continue to move towards the lid 522. Thus, the rigid disks 550, 552 prevent the membrane 510 from being displaced to an extent that the membrane 510 is likely to fail.

The use of the rigid disks 550, 552 allows the disposable portion 500 to withstand higher operating pressures, without causing the thickness of the membrane 510 in the first and second areas 511, 513 to be different than the rest of the membrane 510.

The rigid disk 550 has a ledge portion 550a that is adapted to contact the lid 522, and a central portion, which in one embodiment is a protruding portion 550b, that is adapted to interact with a sensor within the reusable portion 100. Thus, as fluid flows through the disposable portion 500, the first area 511 of the membrane 510 is displaced toward the lid 522, causing the rigid disk 550 to operatively engage or interact with the sensor 120. In one embodiment, the protruding portion 550b passes into or through the opening 524 of the lid 522. However, once the pressure within the upstream chamber 508 reaches a certain level, the ledge portion 550a of the rigid disk 550 contacts the lid 522, preventing further displacement of the first area 511 of the membrane 510.

Similarly, the rigid disk 552 has a ledge portion 552a that is adapted to contact the lid 522, and a central portion, which in one embodiment is a protruding portion 552b, that is adapted to interact with a sensor within the reusable portion 100. Thus, as fluid flows through the disposable portion 500, the second area 513 of the membrane 510 is displaced toward the lid 522, causing the rigid disk 550 to operatively engage or interact with the sensor 122. In one embodiment, the protruding portion 552b passes into or through the opening 526 of the lid 522. However, once the pressure within the downstream chamber 510 reaches a certain level, the ledge portion 552a of the rigid disk 552 contacts the lid 522, preventing further displacement of the second area 513 of the membrane 510.

Therefore, the membrane 510 may be subjected to much higher pressure before failing based on the rigid disks 550, 552 limiting the displacement of the membrane 510.

As shown in FIGS. 4-5, the fluid pressure membrane 510 is a flexible diaphragm type membrane. The fluid pressure membrane 510 may be formed from silicone, or some other flexible polymeric material or elastomeric material. In FIGS. 4-5, the membrane 510 may have a depression or recess formed at the first and second areas 511, 513 in order to allow the rigid disks 550, 552 to be positioned between the membrane 510 and the lid 522.

It is contemplated that a variety of materials may be utilized for the manufacture of the disposable portion 500. The disposable portion 500 may comprise a thermoplastic. It is contemplated that the flow restricting element 512 may be made of the same thermoplastic as the rest of the disposable portion 500, or may be a different material than the disposable portion 500. Non-limiting examples of the material that may be utilized to form the flow restricting element 512 include silicon, glass, and medical grade thermoplastics and elastomers. The flow restricting element 512 even can be made in whole or in part of stainless steel. A stainless steel orifice plate can be encased in a thermoplastic or elastomeric frame. The fluid pressure membranes 510 may comprise a variety of polymeric or elastomeric materials, such as TPE, or silicone.

As shown in FIG. 5, medication enters the disposable portion 500 through the fluid inlet 506. The medication flows into the upstream fluid chamber 508 from the fluid inlet 506. Next, the medication flows through the flow restricting element 512 and into the downstream fluid chamber 514. The flow of the medication through the flow restricting element 512 results in a drop in fluid pressure as the fluid flows from the upstream fluid chamber 508 to the downstream fluid chamber 514 through the flow restricting element 512. Thus, during forward fluid flow under normal conditions, the fluid pressure within the upstream fluid chamber 508 is generally greater the fluid pressure within the downstream fluid chamber 514. The fluid pressure within the upstream fluid chamber 508 presses against the first area 511 of the fluid pressure membrane 510, causing the first area 511 of the membrane 510 to press against the rigid disk 550 and cause the disk 550 to press against the upstream fluid pressure sensor 120 at the upstream opening 524 of the lid 522. Similarly, the fluid pressure within the downstream fluid chamber 514 presses against the second area 513 of the fluid pressure membrane 510, causing the second area 513 of the membrane 510 to press against the rigid disk 552 and cause the disk 552 to press against the downstream fluid pressure sensor 122 at the downstream opening 526 of the lid 522. In one embodiment, the disks 550 and 552 have protruding portions 550b, 552b respectively that at least partially extend into the respective openings 524, 526 of the lid 522 to press against the sensors 120, 122.

It will be appreciated that the embodiments of FIGS. 1-3 and FIGS. 4-5 are closely related. The embodiment of FIGS. 1-3 can be considered an incorporation of the separate disk of FIGS. 4-5 as an integrally molded part of the membrane. The disk can be considered to be made up of a reinforcing ring that may include a hole through its center, or may include the raised areas or protruding portions as illustrated in FIGS. 1-5.

Turning now to FIGS. 6a-11b, a variety of ways to form a differential pressure based flow rate sensor by connecting a disposable portion to a reusable portion are shown. In FIGS. 6a-6b, a differential pressure based flow sensor assembly 600 is shown. The flow sensor assembly 600 comprises a disposable portion 602, and a reusable portion 604. The disposable portion 602 is adapted to slide into the reusable portion 604 as shown in FIG. 6b. The disposable portion 602 includes a ledge portion 603, while the reusable portion 604 includes a securing lip 605. The securing lip 605 of the reusable portion is adapted to interact with the ledge portion 603 of the disposable portion 602 to secure the disposable portion 602 to the reusable portion 604.

FIGS. 7a-7b show a clip type connection for a differential pressure based flow sensor assembly 700. The flow sensor assembly 700 comprises a disposable portion 702 and a reusable portion 704. The disposable portion 702 has a ledge portion 703. The reusable portion 704 has a first clip 705a and a second clip 705b. In one embodiment, the clips 705a, 705b are pivotally mounted on the disposable portion and normally biased inwardly toward each other, for example by springs 709 as best seen in FIG. 1. The clips 705a, 705b each have an outwardly inclined surface 706 that is engaged by the disposable portion 702 and a retention surface 707 that retains the disposable portion 702. The clips 705a, 705b are pivotally displaced when the disposable portion 702 is received within the reusable portion 704 (i.e., forcibly inserted into a cavity 710 of the reusable portion 704 in the direction illustrated by the arrow A). The clips 705a, 705b are allowed to pivot back, such that the clips 705a, 705b interact with the ledge portion 703 of the disposable portion 702 to secure the disposable portion 702 within the reusable portion 704.

Figure 8C:
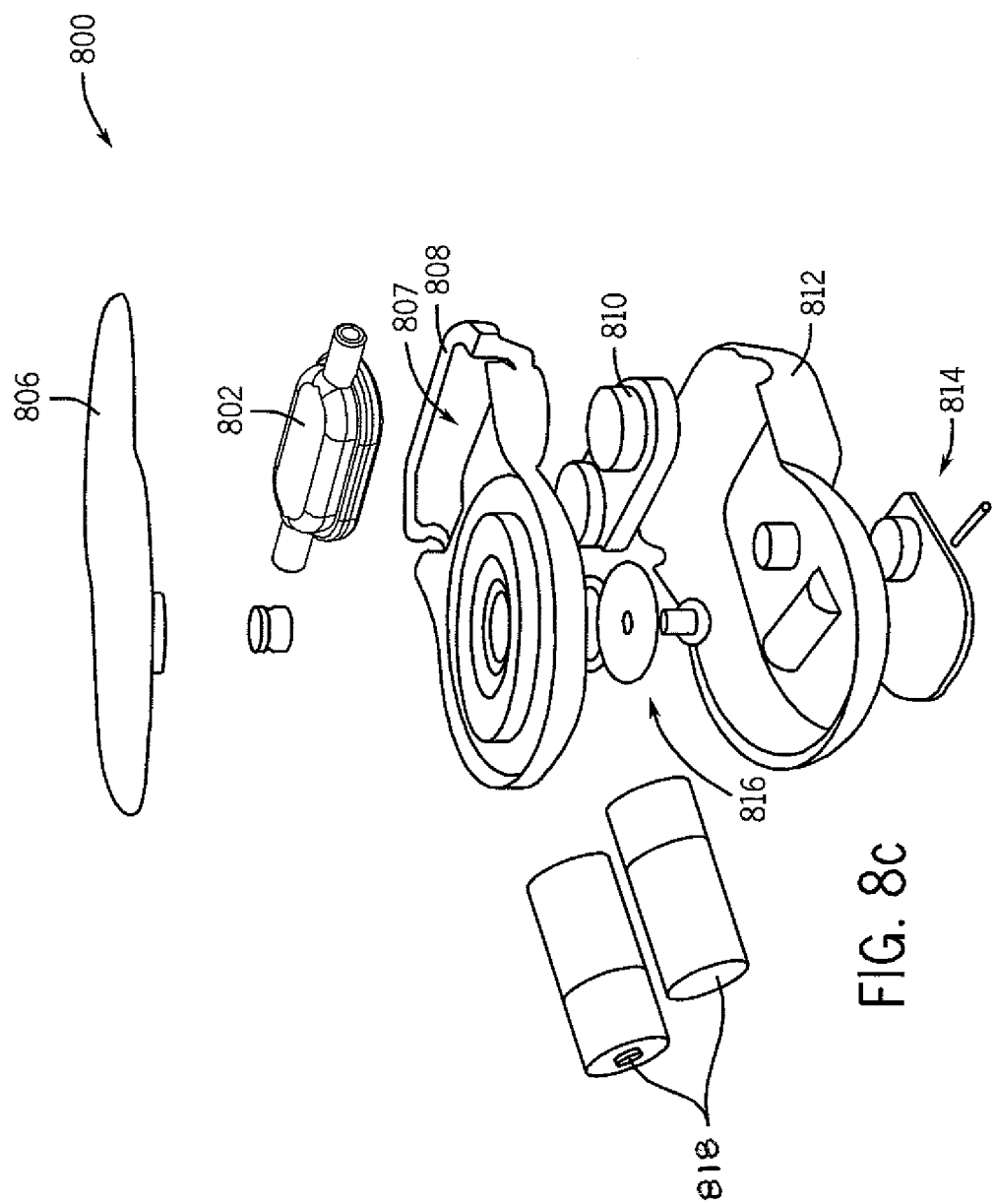

As shown in FIGS. 8a-8c, a differential pressure based flow sensor assembly 800 comprises a disposable portion 802 and a reusable portion 804 that is wireless and has a rotatable cover 806 that secures the disposable portion 802 within the reusable portion. As shown in FIG. 8a, the rotatable cover 806 may be displaced to provide access to the disposable portion 802. As shown in FIG. 8b, the rotatable cover 806 in operation substantially covers the disposable portion 802, securing the disposable portion 802 within the reusable portion 804 of the sensor assembly 800.

FIG. 8c shows an exploded view of the sensor assembly 800. The reusable portion 804 comprises the rotatable lid 806, a tray 808 having a cavity 807 adapted to receive the disposable portion 802, a differential pressure sensor 810, a body 812, a securing clip 814 to allow the flow sensor assembly 800 to be secured to a patient, a rotating mechanism 816 adapted to allow the lid 806 to rotate relative to the body 812, and batteries 818 to provide power to the sensor assembly 800. As the sensor assembly 800 is wireless, the batteries 818 provide power necessary to run the sensor 810 and allow transmission of results from the sensor 810. It is also contemplated that the lid 806 may contain a display to allow the flow sensor assembly 800 to display instantaneous testing results.

Figure 9A:
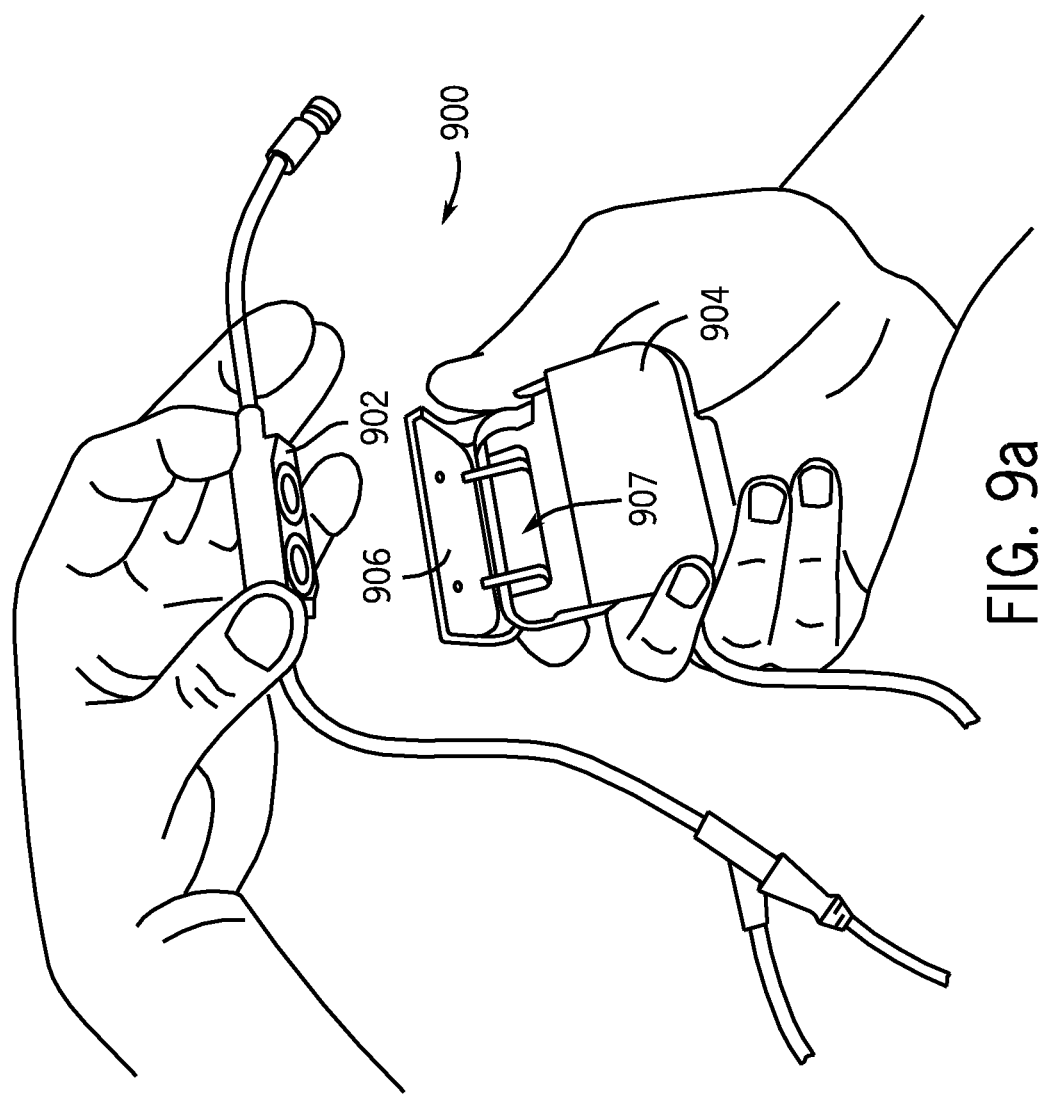
FIG. 9a schematically illustrates a method of assembling a differential pressure based flow sensor assembly according to yet another embodiment.

Turning to FIGS. 9a-9c a differential pressure based flow sensor assembly 900 according to another embodiment is shown. The flow sensor assembly comprises a disposable portion 902 and a reusable portion 904. The reusable portion 904 has an access door 906 that is pivoted to allow the disposable portion 902 to be covered after it is placed within a cavity 907 formed in the reusable portion 904. The disposable portion 902 is adapted to slide or otherwise be placed into the reusable portion 904 with the access door 906 open, as shown in FIG. 9b. The access door 906 may then be closed to secure the disposable portion 902 within the reusable portion 904.

Figure 10A:
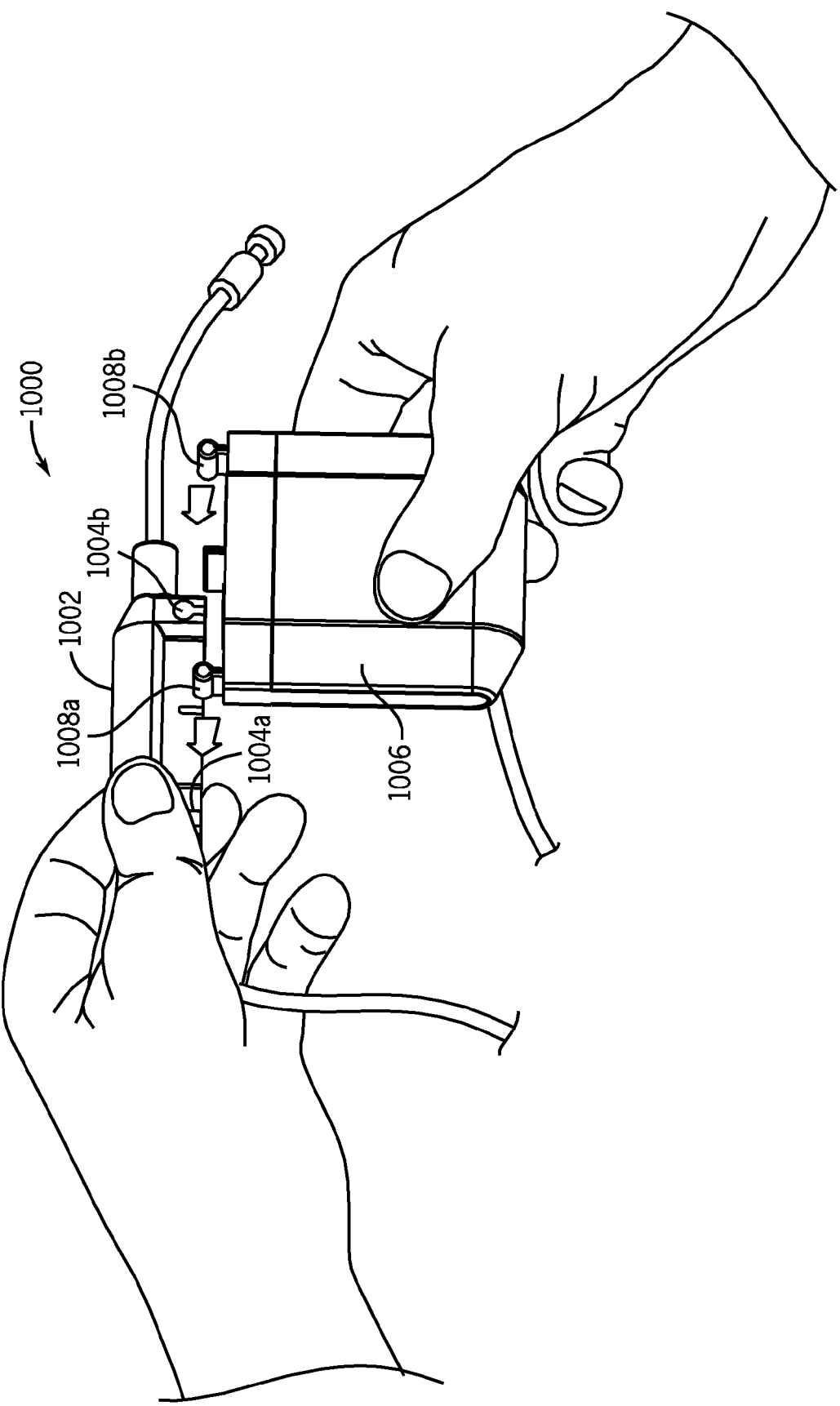
FIG. 10a schematically illustrates a method of assembling a differential pressure based flow sensor assembly according to yet a further embodiment.
Figure 10B:
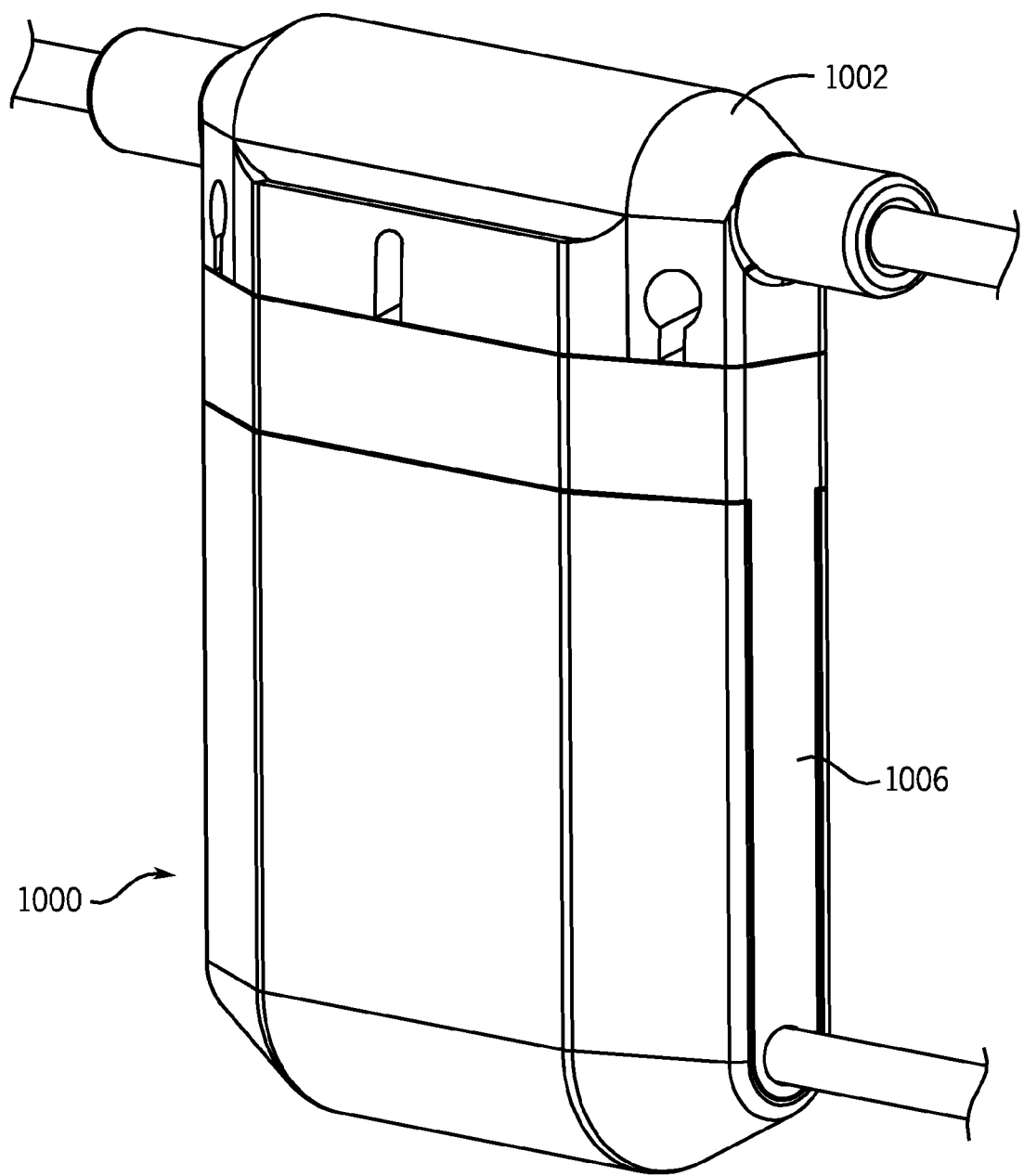

FIGS. 10a-10b show yet a further embodiment of a differential pressure based flow sensor assembly 1000 that comprises a disposable portion 1002 and a reusable portion 1006. The disposable portion 1002 has a first slot 1004a and a second slot 1004b that are respectively adapted to interact with a first securing protrusion 1008a and a second securing protrusion 1008b of the reusable portion 1006. That is, the securing protrusion 1008a resides within the slot 1004a and the securing protrusion 1008b resides within the slot 1004b when the disposable portion 1002 and reusable portion 1006 are assembled to form the flow sensor assembly 1000 as shown in FIG. 10b. While horizontal sliding attachment is illustrated, it is contemplated that the securing protrusions 1008a, 1008b and slots 1004a, 1004b can be adapted to snap together with vertical movement instead.

Figure 11A:
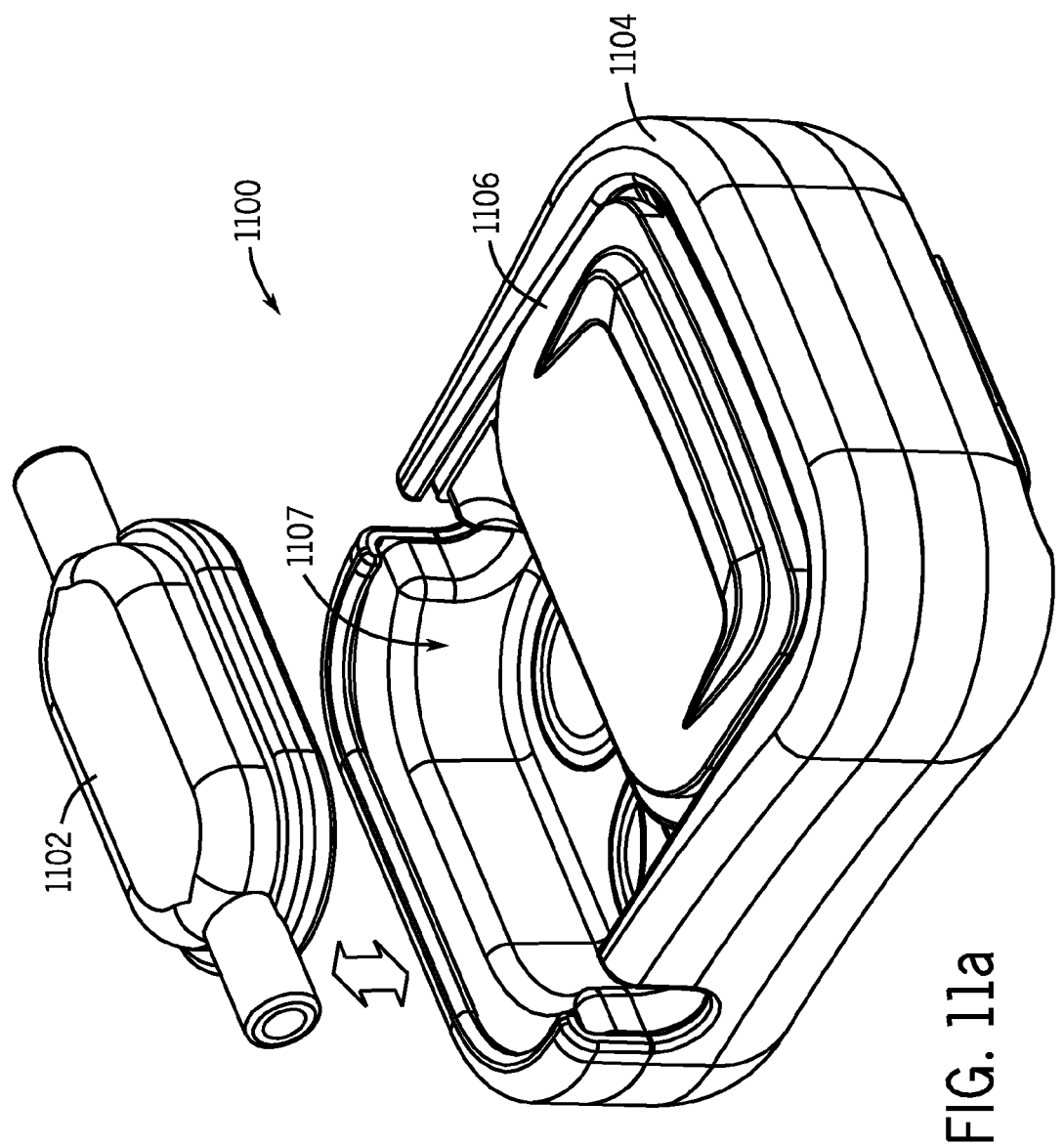
FIG. 11a schematically illustrates a method of assembling a differential pressure based flow sensor assembly according to still yet another embodiment.
Figure 11B:
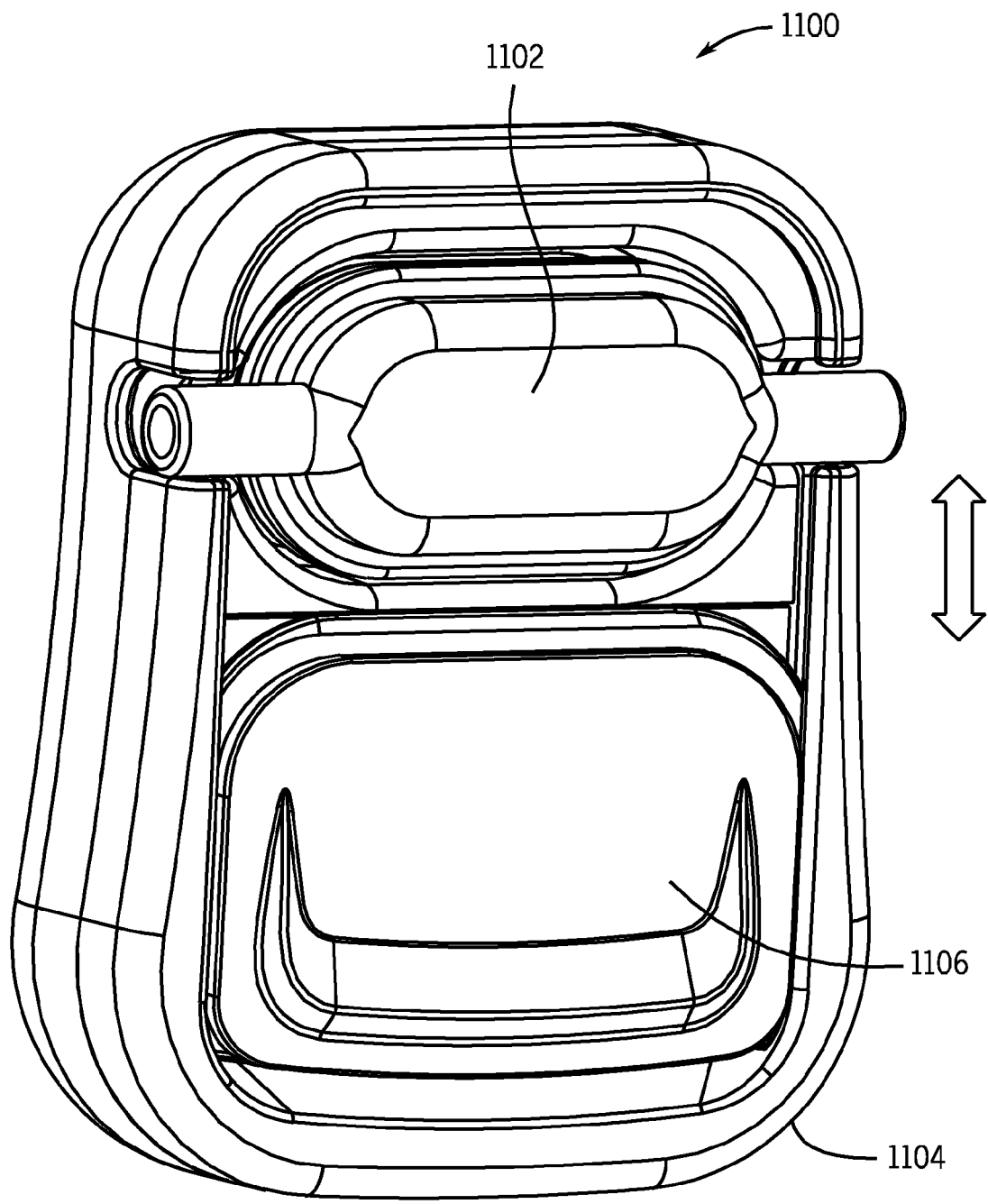
FIG. 11b schematically illustrates an assembled differential pressure based flow sensor assembly according to the embodiment of FIG. 11a with the door open.
Figure 11C:
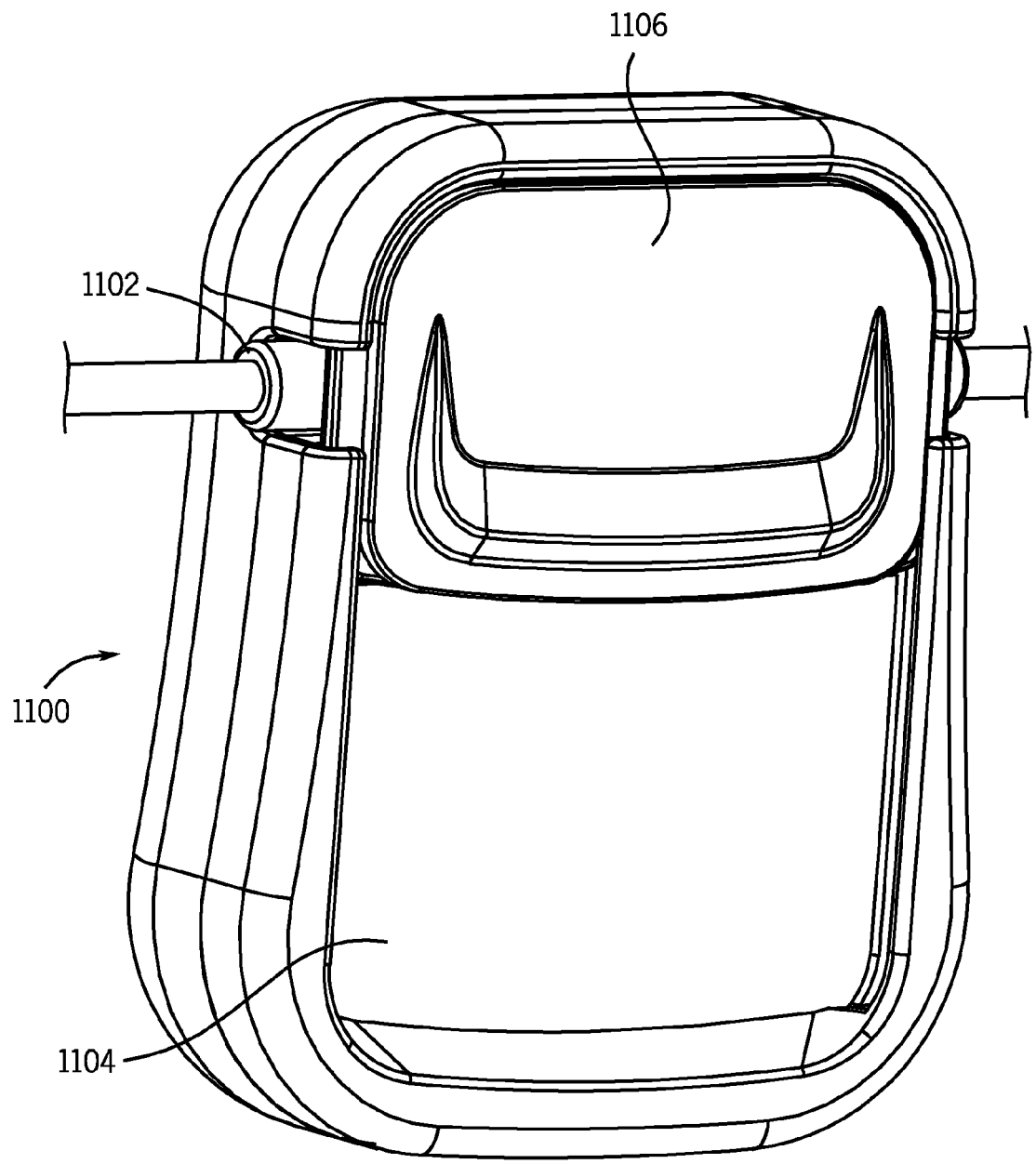
FIG. 11c schematically illustrates an assembled differential pressure based flow sensor assembly according to the embodiment of FIG. 11a with the door closed.

Finally, as depicted in FIGS. 11a-11c a differential pressure based flow sensor assembly 1100 comprises a disposable portion 1102 and a reusable portion 1104. The reusable portion 1104 has a sliding access door 1106. The disposable portion 1102 is placed within a cavity 1107 formed in the reusable portion 1104 as shown in FIG. 11b. The sliding access door 1106 may then be moved to a closed position to secure the disposable portion 1102 within the reusable portion 1104 as shown in FIG. 11c. The flow sensor assembly 1100 is shown as a wireless flow sensor assembly. That is, the results generated by the sensor assembly 1100 are wirelessly transmitted to another device, such as a pump that may control the flow of medication, to allow for a patient's electronic medical record to be updated to show that a fluid was delivered to the patient, as well as the volume of the fluid that was delivered to the patient. It is further contemplated that the reusable portion 1104 may further have a display to show information, such as an instantaneous flow rate, or the volume of fluid delivered.

While the foregoing has described what are considered to be the best mode and/or other examples, it is understood that various modifications may be made and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true scope of the subject matter. Therefore, the subject matter is not limited to the specific details, exhibits and illustrated examples in this description. It is intended to protect any and all modifications and variations that fall within the true scope of the advantageous concepts disclosed herein.

What is claimed is:
1. A method of forming a differential pressure based fluid flow sensor assembly comprising the steps of:
   providing a fluid impermeable reusable assembly having a housing and at least a first pressure sensor and a second pressure sensor mounted in the housing;
   providing a sealed disposable assembly, the disposable assembly comprising:
      a body having a lid portion and a base portion, the body defining a fluid flow passage forming an inlet and an outlet, the lid portion having a first opening and a second opening formed therethrough;
a flow restricting element positioned in the fluid flow passage between the inlet and the outlet and between the first opening and the second opening;
a fluid impermeable flexible fluid pressure membrane disposed along the fluid flow passage and located and sealingly captured between the lid portion and the base portion of the body, the fluid pressure membrane defining a first movable pressure responsive wall portion that sealingly covers a first chamber of the fluid flow passage at a location upstream of the flow restricting element and moves with respect to the first opening in response to fluid pressure within the first chamber and defining a second movable pressure responsive wall portion that sealingly covers a second chamber of the fluid flow passage at a location downstream of the flow restricting element and moves with respect to the second opening in response to fluid pressure within the second chamber, the fluid pressure membrane having a first area aligned with the first opening of the lid portion and a second area aligned with the second opening of the lid portion;
a first rigid disk positioned in the first area on an upper surface of the first movable pressure responsive wall portion of the fluid pressure membrane and having a ledge extending under the lid portion adjacent to the first opening formed in the lid portion, the ledge of the first rigid disk being adapted to contact the lid portion to limit displacement of the first rigid disk and thereby the fluid pressure membrane; and
a second rigid disk positioned in a second area on an upper surface of the second movable pressure responsive wall portion of the fluid pressure membrane and having a ledge extending under the lid portion adjacent to the second opening formed in the lid portion, the ledge of the second rigid disk being adapted to contact the lid portion to limit displacement of the second rigid disk and thereby the fluid pressure membrane;
placing the first rigid disk in the first area on the upper surface of the first movable pressure responsive wall portion and placing the second rigid disk in the second area on the upper surface of the second movable pressure responsive wall portion respectively:
placing the fluid pressure membrane and the flow restricting element in the base portion;
placing the lid portion over the fluid pressure membrane;
joining the lid portion and the base portion together in a sealed manner so as to sealingly capture the fluid pressure membrane between the lid portion and the base portion such that the first rigid disk and the second rigid disk are also captured between the base portion and the lid portion; and
securing the disposable assembly to the housing of the fluid impermeable reusable assembly in a removable manner to form a differential pressure based fluid pressure sensor assembly that does not leak when the disposable assembly is removed from the reusable assembly.

2. The method of claim 1, wherein the step of securing the disposable assembly to the reusable assembly includes sliding a ledge portion of the disposable assembly under a lip portion of the reusable assembly.

3. The method of claim 1, wherein the step of securing the disposable assembly to the reusable assembly includes clipping a ledge portion of the disposable assembly under at least one clip portion of the reusable assembly.

4. The method of claim 1, wherein the step of securing the disposable assembly to the reusable assembly includes covering the disposable assembly under a rotatable lid portion of the reusable assembly.

5. The method of claim 1, wherein the step of securing the disposable assembly to the reusable assembly includes sliding the disposable assembly into the reusable assembly and covering the disposable portion with a pivotable access door to secure the disposable assembly within the reusable assembly.

6. The method of claim 1, wherein the step of securing the disposable assembly to the reusable assembly includes sliding a first slot and a second slot of the disposable assembly over respective first and second securing protrusions of the reusable assembly.

7. The method of claim 1, wherein the step of securing the disposable assembly to the reusable assembly includes positioning the disposable assembly within the reusable assembly and covering the disposable assembly under a sliding access door of the reusable assembly.

8. The method of claim 1, wherein the step of placing the first rigid disk and the second rigid disk on the upper surface of the first movable pressure responsive wall portion and the upper surface of the second movable pressure responsive wall portion respectively comprises molding the first rigid disk and the second rigid disk integrally with the fluid pressure membrane.

* * * * *